(12) United States Patent
Caubel et al.

(10) Patent No.: US 10,495,573 B1
(45) Date of Patent: Dec. 3, 2019

(54) INSTRUMENT FOR MEASURING AIRBORNE PARTICULATE MATTER

(71) Applicants: Julien J. Caubel, Emeryville, CA (US); Troy E. Cados, Orinda, CA (US); Thomas W. Kirchstetter, Berkeley, CA (US)

(72) Inventors: Julien J. Caubel, Emeryville, CA (US); Troy E. Cados, Orinda, CA (US); Thomas W. Kirchstetter, Berkeley, CA (US)

( * ) Notice: Subject to any disclaimer, the term of this patent is extended or adjusted under 35 U.S.C. 154(b) by 0 days.

(21) Appl. No.: 16/007,513

(22) Filed: Jun. 13, 2018

(51) Int. Cl.
*G01N 21/61* (2006.01)

(52) U.S. Cl.
CPC ................................. *G01N 21/61* (2013.01)

(58) Field of Classification Search
CPC ............. G01N 33/5061; G01N 33/566; G01N 1/2273; G01N 2030/121; G01N 2030/3076; G01N 35/00732; G01N 2030/3015; G01N 2035/00782; G01N 21/031; G01N 33/54373; G01N 33/585; G01N 15/02; G01N 15/06; G01N 1/12; G01N 1/26; G01N 2001/1031; G01N 2015/0046; G01N 2015/1486; G01N 2030/642; G01N 21/0303; G01N 21/05; G01N 27/3273; G01N 30/6095; G01N 33/0063; G01N 19/10; G01N 2021/052; G01N 2021/1704; G01N 2021/3181; G01N 2021/3513; G01N 2021/399; G01N 2021/6469; G01N 2033/4975; G01N 21/0332; G01N 21/27; G01N 21/314; G01N 21/33;

(Continued)

(56) References Cited

U.S. PATENT DOCUMENTS

| 4,893,934 A | 1/1990 | Hansen |
| 4,907,166 A * | 3/1990 | Corenman ............. A61B 5/083 600/532 |

(Continued)

OTHER PUBLICATIONS

Bond et al., Calibration and Intercomparison of Filter-Based Measurements of Visible Light Absorption by Aerosols, Aerosol Science and Technology (Online Journal), Jun. 6, 1999, pp. 582-600, vol. 30 Issue 6, Taylor & Francis, Inc., published online: http://www.tandfonline.com/loi/uast20.

*Primary Examiner* — Michael P Stafira
(74) *Attorney, Agent, or Firm* — Theodore J. Bielen, Jr.

(57) ABSTRACT

An apparatus for measuring the optical absorption of airborne matter or other light absorbing species in a sample airflow. The apparatus comprises a flow path through a fibrous filter to collect light absorbing species in the sampled air. The filtered airflow may subsequently pass through a second filter, used for reference measurements. At least one light source impinges in the filter generating one or two optical signals to determine the light absorption of particulate matter or other species in the sampled airflow. The apparatus includes at least one auxiliary sensor in the sample flow path to monitor an environmental factor, such as temperature. During a training period, a mathematical model of the apparatus' environmental sensitivity is derived. Using the mathematical model and measurements from the auxiliary sensor, optical signals are compensated in real time to increase the precision and accuracy of light absorption measurements recorded under fluctuating environmental conditions.

18 Claims, 8 Drawing Sheets

(58) Field of Classification Search
CPC .. G01N 21/3504; G01N 21/39; G01N 21/645; G01N 21/6486; G01N 2201/0612; G01N 2201/062; G01N 2201/0627; G01N 2291/0215; G01N 25/482; G01N 27/3274; G01N 27/416; G01N 29/02; G01N 30/466; G01N 33/004; G01N 33/0075; G01N 33/497; G01N 11/02; G01N 15/0205; G01N 15/0618; G01N 15/065; G01N 15/0656; G01N 15/1056; G01N 15/1404; G01N 15/1459; G01N 15/1484; G01N 1/10; G01N 1/16; G01N 1/2042; G01N 1/2202; G01N 1/2205; G01N 1/40; G01N 2001/1056; G01N 2001/2223; G01N 2001/2276; G01N 2015/0065; G01N 2015/008; G01N 2015/1006; G01N 2015/1081; G01N 2015/142; G01N 2015/149; G01N 2030/0095; G01N 2030/085; G01N 2030/123; G01N 2030/128; G01N 2030/3061; G01N 2035/00465; G01N 2035/0097; G01N 21/274; G01N 21/31; G01N 21/63; G01N 21/79; G01N 25/22; G01N 27/64; G01N 30/08; G01N 30/12; G01N 30/20; G01N 30/30; G01N 30/461; G01N 30/468; G01N 30/52; G01N 30/6039; G01N 31/228; G01N 33/0006; G01N 33/0011; G01N 33/0037; G01N 33/5091; G01N 33/52; G01N 33/574; G01N 33/66; G01N 33/6893; G01N 35/00594; G01N 35/085; G01N 35/1095; G01N 35/1097; G01N 5/02; G01J 3/108; G01J 3/433; G01J 1/0418; G01J 1/0474; G01J 1/0488; G01J 1/4204; G02B 5/0242; G02B 5/208; G02B 5/223; G02B 6/12007

See application file for complete search history.

(56) References Cited

U.S. PATENT DOCUMENTS

| | | | |
|---|---|---|---|
| 5,042,522 A * | 8/1991 | Corenman | A61B 5/083 137/239 |
| 7,038,765 B2 | 5/2006 | Petzold et al. | |
| 9,018,583 B2 | 4/2015 | Mocnik et al. | |
| 2014/0260692 A1* | 9/2014 | Sharp | G01N 1/2273 73/863.23 |
| 2016/0349175 A1 | 12/2016 | Blair et al. | |
| 2017/0370809 A1 | 12/2017 | Miller-Lionberg et al. | |

* cited by examiner

INSTRUMENT FOR MEASURING AIRBORNE PARTICULATE MATTER

STATEMENT REGARDING FEDERALLY SPONSORED RESEARCH OR DEVELOPMENT

The present application was made with Government support under contract DE-ACO2-05CH11231 awarded by the United States Department of Energy. The Government has certain rights in the application.

CROSS-REFERENCES TO RELATED APPLICATIONS

The present application claims the benefit of U.S. Provisional Application No. 62/526,237 filed 28 Jun. 2017 and U.S. Provisional Application No. 62/526,770 filed 29 Jun. 2017.

BACKGROUND OF THE INVENTION

The present application relates to an instrument and method for determining the optical absorption of matter, including black carbon, in the atmosphere.

Black carbon (BC), or soot, is a primary light-absorbing component of particulate matter generated by biomass and fossil fuel combustion. BC is extremely harmful to both human health and the environment. It has been estimated that airborne particulate matter, including BC, kills an estimated 4 million people per year worldwide. In addition, BC is the second largest contributor to global warming after carbon dioxide. In order to assess BC's impact on climate and human populations, it is necessary to measure both the geographical and vertical distribution of BC in the atmosphere on a large scale.

In the past, an instrument known as an Aethalometer has been employed to measure the concentration of optically absorbing ("black") suspended particulates in a gas. Such airborne particulate matter (PM) is commonly visualized as smoke or haze and is often seen in ambient air under polluted conditions. Current Aethalometers or BC instruments are usually large bench-top units and are quite expensive to acquire. Furthermore, current BC instruments are not designed to be deployed outdoors and, thus, perform poorly in fluctuating ambient conditions.

In the past, BC instruments have been devised. For example, U.S. Pat. No. 4,893,934 describes an Aethalometer having a single light source and a single light detector that produces two light paths. A filter collects particles from ambient air in a collection area. A rotating disc allows light from a source to pass alternately through the two light paths and, thus, through the collection and reference areas of the filter. The intensity of light transmitted through the filters are measured and compared to determine the absorption coefficient of the aerosol particles collected on the filter.

U.S. Pat. No. 7,038,765 describes an apparatus and method for measuring black carbon in the atmosphere which utilizes a filter tape that is continually illuminated by a source. Light absorbing aerosol material collected on the tape is continually determined from changes in the optical properties of the tape collection areas, with the aid of known algorithms.

U.S. Pat. No. 9,018,583 shows a method for automatically diagnosing and calibrating a photometric particle analyzer that employs a trio of sensors receiving light from a light source through a filter having a collection and reference portion to produce first and second signals. A third sensor produces a third signal without passing through the filter. Thus, baseline and test measurement comparisons are obtained to provide a diagnostic of the operation of the photometric particle analyzer.

An article entitled "Calibration and Intercomparison of Filter Based Measurements of Visible Light Absorption By Aerosols", Aerosol Science and Technology, Vol. 30, pp. 582-600, 1999, Bond et al., shows an analyzer where the differences between sequential optical measurements are used to estimate particular concentrations of various types.

United States Patent Publication 2016/0349175 teaches an apparatus receiving an analyte in which two housing portions are clamped together sandwiching a substrate to which analyte is delivered. Optical signals of various wavelengths are passed through the substrate to study analyte properties and are analyzed by optical sensors.

United States Patent Publication 2017/0370809 shows a portable air sampling device that utilizes a filter receiving and trapping airborne particles. The average mass concentration of aerosol collected by the filter is determined using gravimetric analysis.

A low cost, compact instrument for measuring the optical absorption of and concentration of matter, such as particulate black carbon pollutants and other analytes, is needed. Such an instrument should be easy deployed on a massive scale to measure BC distributions both on the ground and in the atmosphere, accurately and reliably under fluctuating environmental conditions.

SUMMARY OF THE INVENTION

In accordance with the present application, a novel and useful instrument for measuring the optical absorption of airborne matter, such as a black carbon particulates, is herein provided.

The instrument or detector of the present application passes a sample of air through a fibrous filter and measures the attenuation of the light through the filter as light absorbing matter, such as BC particles, are deposited. This attenuation in light intensity can be directly correlated to volumetric BC mass concentrations in the sampled airflow. The detector also utilizes a bank of light emitting diodes (LEDs) that project light through two separate orifices in the filter material and onto two corresponding photodiodes. These two photodiodes generate electrical voltages representing a sample and a reference, respectively. The sample and reference voltages are proportional to the intensity of light passing through the filter at each orifice.

A vacuum pump is used to draw ambient air through the instrument or detector. Such sampled air first passes through the signal orifice, trapping suspended particles on the filter and creating a deposit of increasing density. The beam of light from the LEDs is attenuated by BC particles trapped on the filter. After passing through the signal orifice, sample air flows through the reference orifice. Since the air passing through the reference orifice is filtered, such air does not contain aerosol particles and the light intensity passing through the reference filter remains unaffected by BC concentrations. The light intensities of the attenuated light passing through the BC deposit and the reference light are measured by two photodiodes that are correlated to BC concentrations in the air sample using Beer Lambert's Law.

It should be realized that the reference light's intensity is equally affected by other factors such as temperature and relative humidity in the sampled air. The detector of the present invention uses the reference signal generated by airflow recirculation through the reference filter to compensate measurements for environmental fluctuations. Also, measurement deviations resulting from temperature fluctuations are further corrected using a temperature sensor mounted at the sample flow inside the optical cell. The instrument is operated during a training period, and the measurements collected are used to derive a mathematical model of the instrument's temperature sensitivity. This model is uploaded to the instrument's onboard MCU, and light absorption measurements are compensated in real time by use of such onboard temperature sensor. Through an algorithm, the instrument's temperature dependence is characterized prior to deployment and subsequently corrected in real time by use of such onboard temperature sensor.

In addition, the detector of the present application is designed with a short unobstructed path for the flow of sampled air. This flow path allows for greater airflow rates to be pumped through the instrument, requiring less power and, consequently, leading to an increase in the effective sensitivity to BC concentrations.

Since air flow and optical pathways are identical for the reference and signal orifices, the flow path of sampled air may be reversed, allowing clean, reference portion of the filter to be used for aerosol particle collection, and the fouled sample filter to serve as the reference. This roughly doubles the amount of time that the instrument can operate prior to replacement of the aerosol filter.

The instrument may be designed as a compact, monolithic unit that interfaces with a micro-controller using a minimum number of connections. In addition, all components of the instrument may be mounted on a single printed circuit board. The result is a compact instrument that can be easily packaged for a wide variety of application and interfaced easily with other instruments, hardware components, and software protocols.

It may be apparent that a novel and useful aerosol black carbon detector or instrument has been hereinabove described.

It is therefore an object of the present application to provide an aerosol black carbon detector that is compact and inexpensive.

Another object of the present application is to provide an aerosol black carbon detector that may be easily incorporated into both terrestrial and airborne instrument platforms to measure atmospheric BC concentrations.

Another object of the present application is to provide an aerosol black carbon detector or instrument that incorporates both hardware and software features that actively compensate light absorption measurements for environmental factors, such as temperature. Thus, such instrument allows for more accurate measurements when deployed in the wide range of atmospheric conditions encountered from the ground surface to high altitudes.

Another object of the present application is to provide an aerosol black carbon detector that is specifically designed to provide BC measurements on a large scale to allow users to better understand and mitigate the impact of BC pollutants on humans and on the environment in general.

Another object of the present application is to provide an aerosol black carbon detector that includes an "active reference cell", a reference orifice sampling filtered air, minimizing sensitivity to relative humidity and temperature variations.

Another object of the present application is to provide an aerosol black carbon detector that includes a sample flow path which is capable of accommodating high sample flow rates and, thus, increases measurement sensitivity.

Another object of the present application is to provide an aerosol black carbon detector that utilizes an auxiliary sensor to measure temperature, humidity, or other environmental factors to compensate for such detector's inherent sensitivity to these factors in real time, thereby increasing the precision and accuracy of desired light absorption measurements.

Another object of the present application is to provide a method for characterizing a black carbon detector's dependence on environmental factors, such as temperature or relative humidity.

Another object of the present application is to provide an aerosol black carbon detector that is of robust design and is easily manufactured and maintained.

A further object of the present application is to provide an aerosol black carbon detector that is compact in size and is easily incorporated into airborne vehicles such as high altitude balloons, ground vehicles, or backpacks carried by humans.

A further object of the present application is to provide an aerosol black carbon detector that is symmetrically arranged to allow reversal of a sample air path to reduce maintenance.

The invention possesses other objects and advantages especially as concerns particular characteristics and features thereof which will become apparent as the specification continues.

For a better understanding of the application, reference is made to the following detailed description of the preferred embodiments thereof which should be referenced to the prior described drawings.

DETAILED DESCRIPTION OF THE PREFERRED EMBODIMENTS

Various aspects of the application will evolve from the following detailed description of the preferred embodiments thereof which should be taken in conjunction with the prior delineated drawings.

The embodiments of the apparatus of the present application are identified by reference character 10 followed by an uppercase letter to denote variations.

Figure 1:
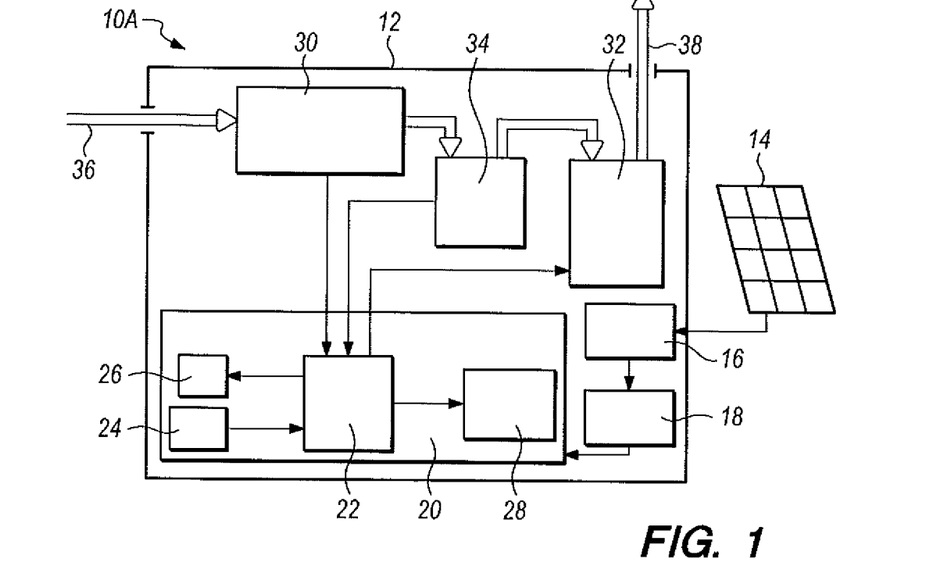
FIG. 1 is a schematic view of the detector apparatus of the present application.

In FIG. 1, detector apparatus 10A is shown as being employed with an enclosure or case 12 which may be a weatherproof, insulated box. A photovoltaic panel 14 may be mounted to enclosure 12 and provide electrical power to apparatus 10A, typically 18 volts, 8-watts. Photovoltaic panel 14 sends electrical power to charge controller 16 which in turn passes power to battery 18. An integrated electronics board, AUX board 20, receives electrical power from battery 18 for use with the electrical components found on AUX board 20. For example, AUX board 20 includes a microcontroller unit (MCU) 22, real time clock 24, an SD memory card slot 26, and a 2G cellular modem 28. In addition, AUX board 20 possesses conventional power management electronics and necessary hardware for required input and output connections. Needless to say, MCU 22 processes and stores data to the SD memory card and is typically programmed at two second intervals, although measurement intervals greater or equal to one second may be employed. The 2G cellular modem 28 is capable of transmitting data and is typically programmed to transmit 60 one-minute average values every hour to an online database. An optical cell 30 is also found within enclosure 12 and will be more fully discussed as the specification continues.

A vacuum pump 32 delivers ambient air samples to optical cell 30. The pump 32 may take the form of a rotary vane pump, although other pumps would suffice. The flow rate of air sampled through apparatus 10A is measured using an air flow or differential pressure sensor 34. For example, differential pressure sensor 34 may entail an Omron D6F mass flow sensor. In any case, sample air enters enclosure 12 as inlet air stream 36 and exits the same as outlet air stream 38.

Air flow sensor 34 outputs an analog voltage that is dependent on the mass flow rate of air therethrough. Such data is sent to MCU 22. To calibrate air flow sensor 34, the analog voltage output is recorded while the sample air stream 36 flow rate is simultaneously measured. A pulse-width modulated signal is generated by MCU 22 to control the electrical power delivered to pump 32. In the present configuration, the desired flow rate of pump 22 may be set to anywhere between 100 ccm and 250 ccm.

Figure 2:
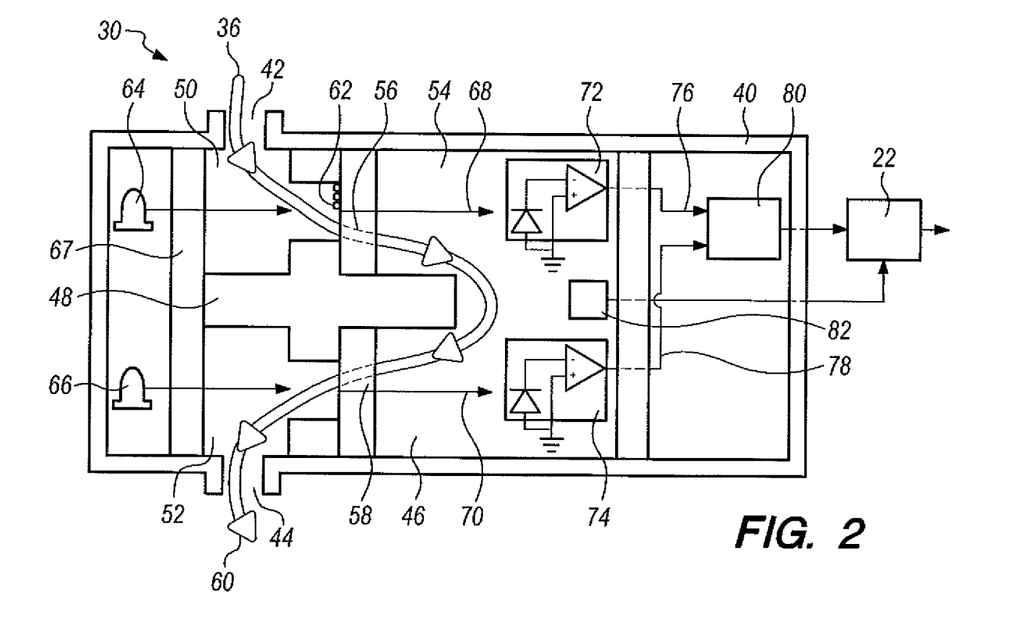
FIG. 2 is a schematic view of the optical cell portion shown in FIG. 1.

Turning now to FIG. 2, it may be observed that optical cell 30 is shown in greater detail. Optical cell 30 is found in a case 40 having an air sample inlet 42 and an air sample outlet 44. Thus, case 40 includes a chamber 46. Partition 48 lies within chamber 46 and forms subchambers 50, 52, and 54. Optical cell 30 is also provided with a first filter 56 and a second filter 58 lying apart from first filter 56. Filters 56 and 58 lie within orifices, shown schematically in FIG. 2. Filters 56 and 58 may take the form of Teflon-coated glass-fiber filters, such as Pallflex Emfab filters. Other filters such as quartz fiber filters may also be used. Filter 56 traps particulate matter, such as black carbon, in airstream 36 and is referred to as the sample filter. Filter 58 receives sample air stream 36 and passes a clean air stream 60 therefrom.

Filter 58 is referred to as the reference filter. Air reaching reference filter 58 is substantially free of black carbon since filters 56 and 58 have a particle removal efficiency of 99.9%. As shown in FIG. 2, black carbon deposits 62 are found on sample filter 56. When sample filter 56 reaches a high optical attenuation value, filters 56 and 58 are replaced.

Optical cell 30 is also fashioned with light emitting diodes (LEDs) 64 and 66. LED 64 passes light through translucent member 67 and sample filter 56 such that light ray 68 is attenuated by the presence of BC deposits 62. On the other hand, light ray 70 passes through reference filter 58 and is unaffected by BC concentrations in sample air stream 36, air stream 60 being filtered as heretofore described. LEDs 64 and 66 may operate at a central wavelength of 880 nm, where black carbon is the predominant species to absorb light. However, light at any wavelength may be employed according to the particular species being analyzed. A sample light ray 68 and a reference light ray 70 pass to photodiodes 72 and 74. Photodiodes 72 and 74 measure the intensity of the sample and reference light rays 68 and 70, respectively, and produce voltage signals 76 and 78 that are linearly proportionally to the intensity of light transmitted through filters 56 and 58, respectively. Where multiple wavelength light is used, photodiodes 72 and 74 may take the form of spectrometers. An analog-to-digital converter (ADC) 80 digitizes voltage signals 76 and 78 and sends the same to MCU 22.

A relative humidity and/or temperature (RH/T) sensor 82 is mounted directly in subchamber 54 directly in the flow path of air stream 60 adjacent the sample photodiode 72 and the reference photodiode 74. RH/T sensor 82 provides measurements required to compensate apparatus 10A for environmental measurements artifacts to MCU 22, which will be discussed in greater detail as the specification continues. ADC 80 and MCU 22 provide a proportional value of the sample voltage signal 76 and the reference voltage signal 78. As will be discussed hereinafter, such ratio is then processed to determine the mass concentration of BC in sample air stream 36. Such correlation takes place using Beer Lambert's law.

Figure 3:
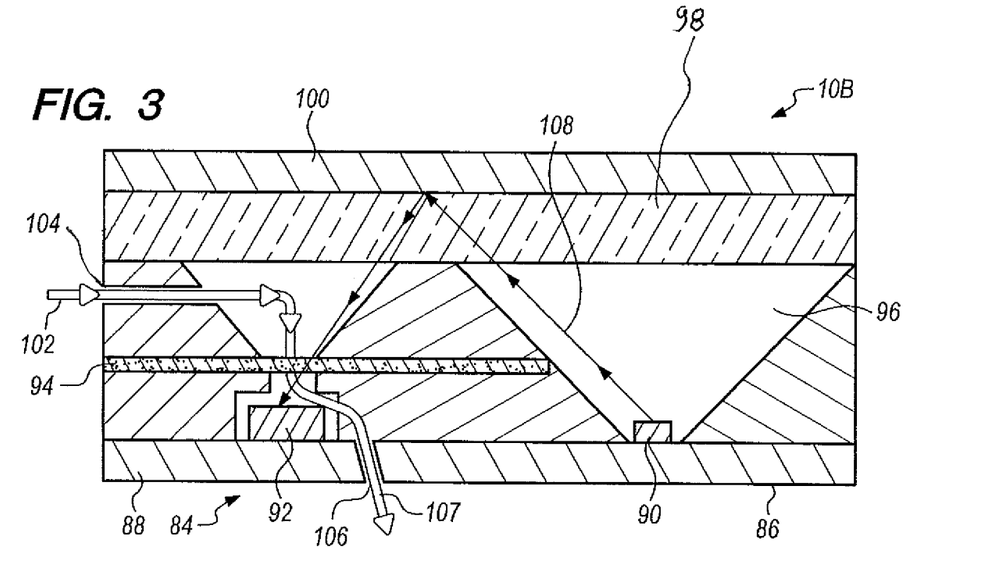
FIG. 3 is a sectional view of an alternate embodiment of the present application.
Figure 4:
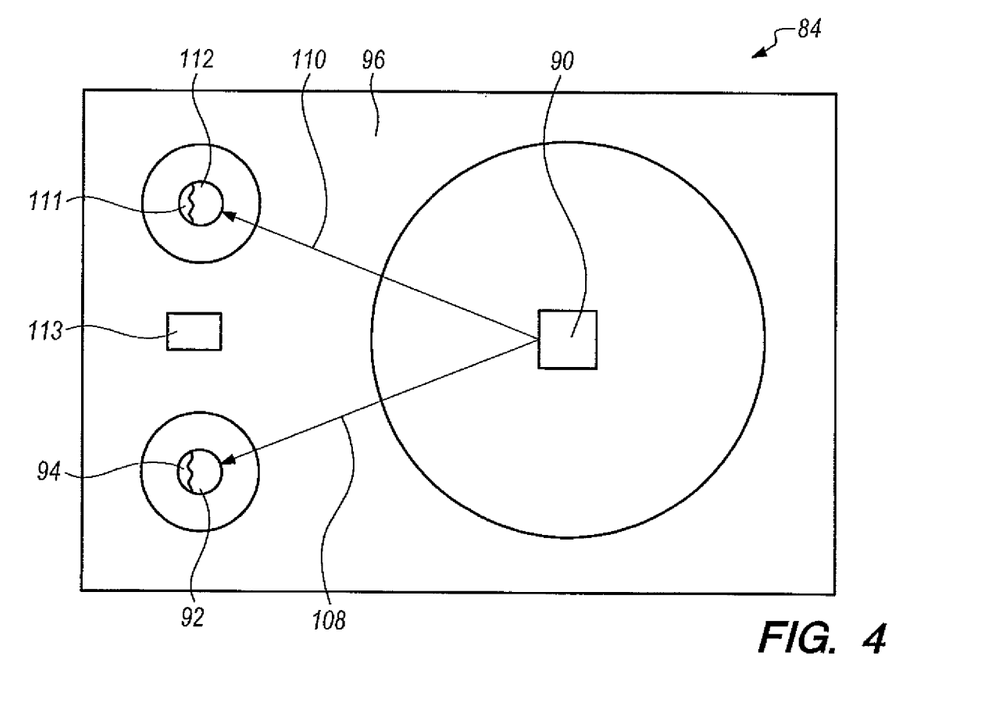
FIG. 4 is a schematic top plan view of the apparatus depicted in FIG. 3, with filters and photodiodes depicted in broken configuration.

Referring now to FIGS. 3 and 4, it may be observed that another embodiment 10B of the apparatus of the present application is shown. Apparatus 10B includes an optical cell 84 that is placed in a case 86 and further includes printed circuit board 88 that serves as a single base or mount for a sole light emitter 90 and a photo detector 92. In certain cases, all the components shown in FIG. 1 may be mounted to a single base such as a PCB. Optical cell 84 also is provided with an aerosol filter 94 which lies adjacent chamber 96 of optical cell 84. In addition, a glass layer 98 is positioned below a reflector 100. Airflow stream 102 passes through inlet 104 of case 86, travels through aerosol filter 94, and flows out of case 86 through outlet 106 as filtered air stream 107. Light path 108 indicates that light originates with light emitter 90, impinges and returns from beam splitting reflector 100, passes through aerosol filter 94, and hits photodetector 92. As described in embodiment 10A of FIGS. 1 and 2, photodetector 92 generates a signal that is indicative of the presence of light absorbing particulate matter such as black carbon on aerosol filter 94. As may be apparent from FIG. 4, light emitter 90 also produces a second light path 110 which hits a filter 111 and photodetector 112 below. RH/T sensor 113 is also found in embodiment 10B. Filtered air stream 107 is passed through filter 111 in the same manner as shown in FIG. 2, with respect to apparatus 10A. Thus, photodetector 112 serves as a source of reference signals. The sample signals from photodetector 92 and the reference signals from photodetector 112 are processed in the same manner as shown in FIGS. 1 and 2 with respect to signals 68 and 70 of apparatus 10A. It should be noted that using a sole light emitter 90 eliminates intensity variation inherent with the dual light emitters of FIGS. 1 and 2.

Figure 5:
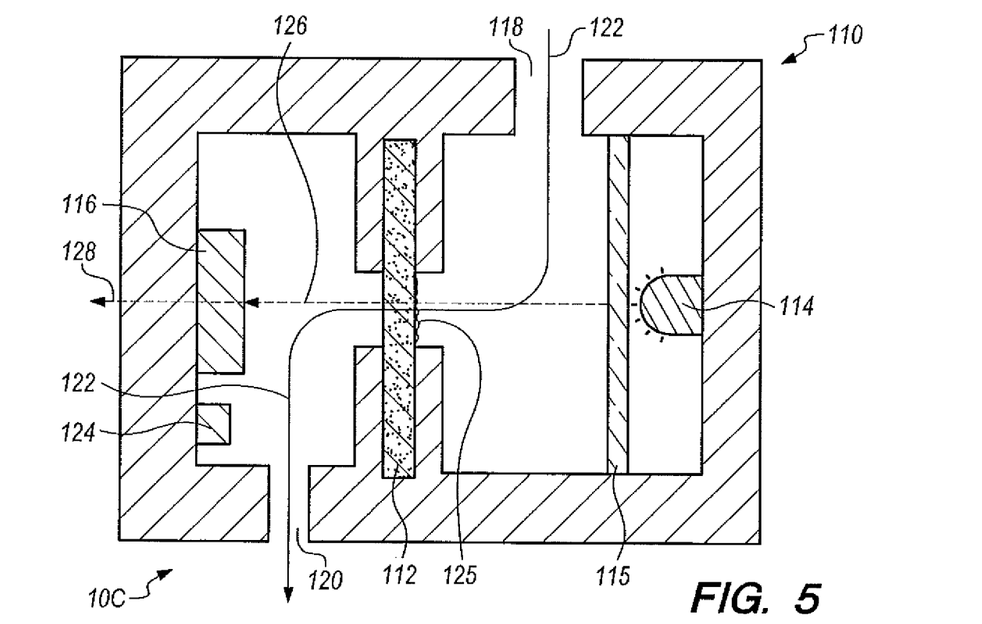
FIG. 5 is a sectional view of another embodiment of the optical cell of the present application.

FIG. 5 illustrates another embodiment 10C of an optical cell of the present application used in lieu of optical cell 30, FIG. 1. A case or housing 110 encompasses a filter 112 which lies between LED 114 and photodetector 116. Housing 110 includes an ambient air inlet 118 and outlet 120. Air path 122 shows the route of air passing through filter 112 and housing 110. Relative humidity/temperature (RH/T) sensor 124 also lies within housing 110 and is used to compensate the environmental factor sensitivity of light absorption measurements from photodetector 116, discussed hereinafter. Light emanating from LED 114 travels via light path 126, through glass 115, filter 112, and impinges on photodetector 116. Light ray 126 is attenuated by BC deposits 125. Light ray 126 transforms into sample signal 128 at photodetector 116. RH/T sensor 124 generates second and third signals. Embodiment 10D has been operated during a "training period", discussed hereinafter. The measurements collected during such "training period" are used to derive a mathematical model of the instrument's RH/T sensitivity.

This model is uploaded to MCU 22, and RH/T measurements are used to compensate light absorption measurements in real time, eliminating the need for the reference LED, filter and photodiode. Essentially, embodiment 10C is immunized from environmental fluctuations using RH/T sensor 122 and the mathematical model. The calculation of BC is based on comparing the value of a current sample signal 128 to the value of a previous sample signal. The previous sample signal value would then serve as a reference value. Again, the temperature dependence of reference components and noise amplification is eliminated in embodiment 10C, as is the case with other embodiments found herein. Also, intensity variation and noise amplification inherent in dual light emitters and dual photodetectors is eliminated.

Figure 6:
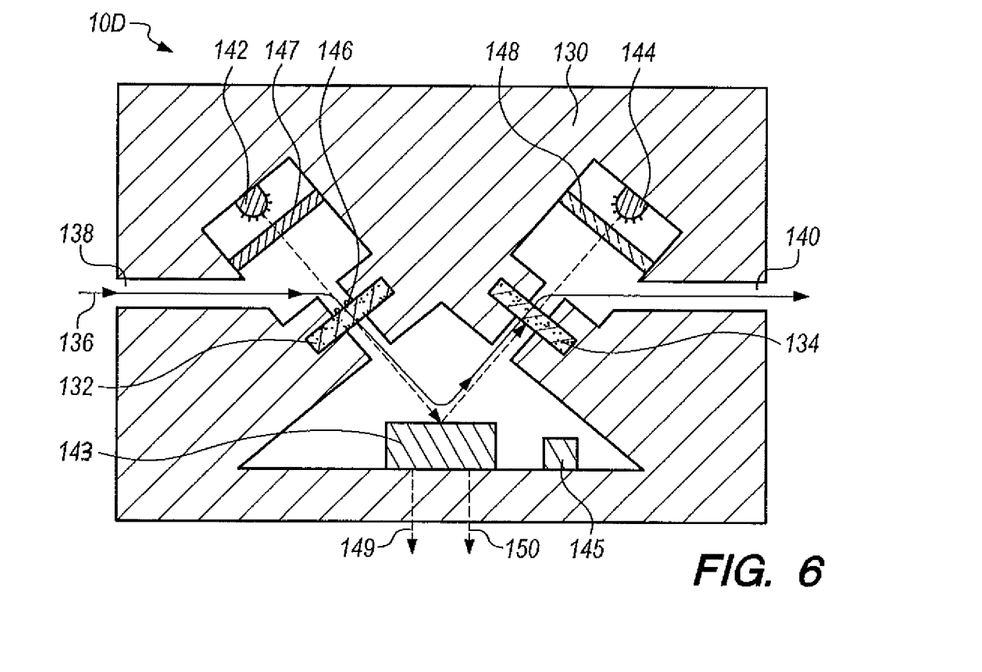
FIG. 6 is sectional view of yet another embodiment of the optical cell of the present application.

FIG. 6 represents yet another embodiment 10D of the present application. A housing 130 encloses sample filter 132 and reference filter 134. Air path 136 extends through housing inlet 138, filters 132 and 134, and to housing outlet 140. LEDs 142 and 144 pass light through glass elements 147 and 148, and filters 132 and 134, to a single photodiode 142. RH/T sensor 145 lies adjacent photodiode 142. BC deposits 146 accumulate on sample filter 132. By alternately turning LEDs 142 and 144 "on" and "off" photodetector 142 will alternately generate sample and reference signals 149 and 150. Again, measurement variation and noise amplification problems are avoided by using a single photodetector. Of course, such sample and reference signals 149 and 150 are processed in the apparatus shown on FIG. 1 where optical cell embodiment 10D is substituted for optical cell 30.

In operation, with reference to FIGS. 1 and 2, air is drawn through chamber 46 of case 40 and initially passes through subchamber 50. At this point, the airflow passes through filter 56 and into second subchamber 54. Under the influence of vacuum pump 32, the airflow stream then travels through uncontaminated filter 58 and out exit 44 of case 40. Air flow sensor 34 downstream of optical cell 30 measures the mass flow rate of air stream 60. MCU 22, through a signal from sensor 34, generates a pulse-width modulated signal to control the electrical power delivered to vacuum pump 32. Thus, a desired flow rate of air stream 36 is maintained through optical cell 30. Light emitting diodes 64 and 66 produce sample and reference light rays 68 and 70, respectively, that travel through sample filter 56 and reference filter 58, respectively. Photodiodes 72 and 74 generate electrical voltages that are linearly proportional to the intensity of light transmitted through sample filter 56 and reference filter 58, respectively. The analog voltage measurements from photodiodes 72 and 74 are digitized using analog-to-digital converter 80 that produces a digital signal processed by MCU 22. MCU 22 eventually determines a ratio of BC mass concentration in air stream 36 through the measured optical attenuation between light rays 68 and 70, which is expressed as the natural log ratio of the reference to sample voltage outputs. The following equation represents such calculation:

$$ATN(t) = 100 * \ln\left(\frac{V_{ref}(t)}{V_{smpl}(t)}\right) * \left(\frac{V_{smpl}(0)}{V_{ref}(0)}\right)$$

where $V_{smpl}(t)$ and $V_{ref}(t)(V)$ are the optical, cell, sample and reference voltage outputs 76 and 78 at each measured time step t, respectively. The Black Carbon mass concentrations ($\mu g/m^3$) at each measurement time interval are calculated based on optical attenuation and flow rate as:

$$BC(t_i) = \frac{A}{Q(t_i) * MAC * (t_i - t_{i_{-1}})} * \ln\left(\frac{ATN(t_i)}{ATN(t_{i_{-1}})}\right) = \frac{A}{Q(t_i) * MAC * (t_i - t_{i_{-1}})} \ln\left(\frac{V_{ref}(t_i)}{V_{smpl}(t_i)} * \frac{V_{smpl}(t_{i_{-1}})}{V_{ref}(t_{i_{-1}})}\right)$$

where $t_{i_{-1}}$ and $t_i$ are the time stamps of two consecutive measurements and A ($m^2$) is the surface area of each filter. The filters 56 and 58 may be placed in orifices that are circular and may typically have a diameter of 0.003175 m and a corresponding area of $7.87 \times 10^{-6}$ $m^2$, although other sized orifices may be employed. Q is the mass flow rate of air stream 36 through optical cell 30 measured by differential pressure sensor 34 which lies downstream of optical cell 30. The flow rate of the air stream 36 through optical cell 30 is typically set between 100 cc/min and 250 cc/min. Flow sensor 34 measures the flow rate. MCU 22 uses this information to modulate the power delivered to pump 32. MAC is the mass attenuation coefficient of BC which is set at 12.5 $m^2/g$ in the present case. However, a different MAC value would be used with a different wavelength of light, or species of interest.

Working Example

Figure 7:
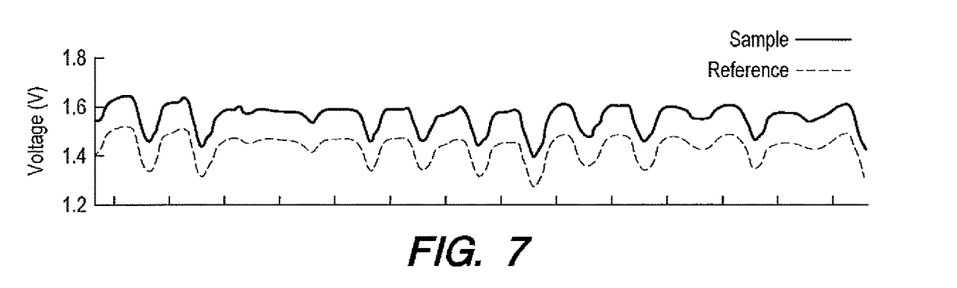
FIG. 7 is a graph depicting voltage outputs from the optical cell depicted in FIG. 2.
Figure 8:
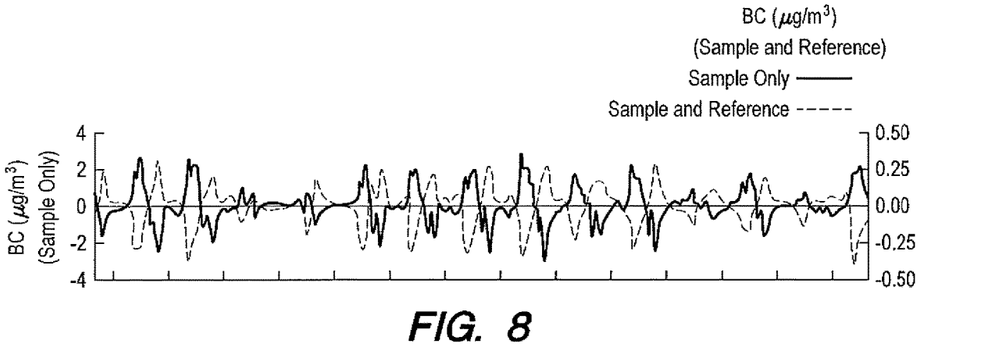
FIG. 8 is a graph showing black carbon concentrations calculated using the apparatus of the present application.
Figure 9:
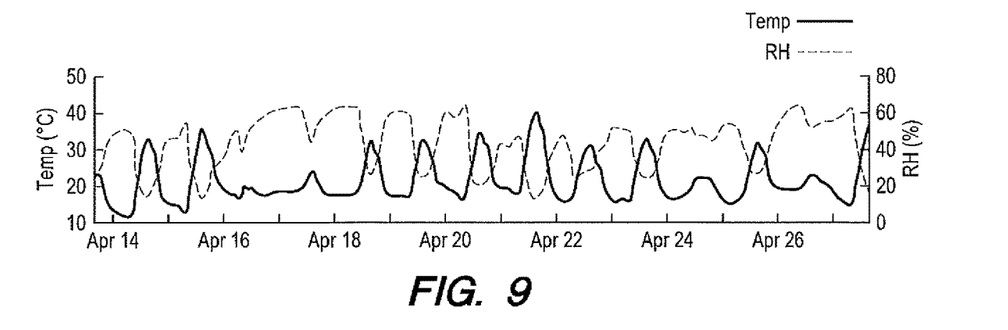
FIG. 9 is a graph depicting temperature and relative humidity measurements over a period of time.

Apparatus 10A was operated outdoors with a High Efficiency Particulate Air (HEPA) filter on inlet 42 for a two week period (a "training" period). FIGS. 7-9 represent data obtained therefrom. FIG. 7 shows that the sample and reference output voltages 76 and 78, FIG. 2, are clearly dependent on ambient conditions, oscillating in sync with the diurnal trends in temperature and relative humidity. FIG. 9 shows such results. It is theorized that the output voltage oscillations shown in FIG. 7 are likely the result of temperature sensitivity of LEDs 64 and 66, FIG. 2. LEDs 64 and 66 are rated to dim 0.3% for every 1° C. temperature rise, which is approximately represented by the observation of FIG. 5. Thus, the temperature sensitivity of LEDs 64 and 66 play a major role in the accuracy of apparatus 10A. Photodiode sensitivity (the voltage output per watt of incident light intensity) decreases by 0.01% for every 1° C. temperature rise, and likely also contributes to the diurnal-nocturnal voltage oscillations. It should also be noted that the measurements of apparatus 10A essentially measure the temperature of the air flowing through optical cell 30, but it is assumed that any electronics associated with device 10A are at a similar temperature. Expected variations in the optical thickness of the filters 56 and 58 due to sorption and desorption of water vapor from air stream 36 are opposite to the observed voltage oscillations. This suggests that the relative humidity sensitivity is smaller than the temperature dependence of the optical electronics of apparatus 10A. It is also noted that measured BC concentrations by apparatus 10A exhibit diurnal trends that are typically in the ±0.3 μg/m³ range. This trend is exhibited in FIG. 6. It should be noted that the BC concentrations computed using only the output from photodiode 64 are much larger and are in the ±2 μg/m³, FIG. 6. Consequently, it follows that computing BC concentrations using both the reference and sample signals 76 and 78 significantly reduces, but does not completely eliminate the sensor's sensitivity to environmental conditions. It is also noted that where BC concentrations are much larger than ±0.3 μg/m³, then further compensation may not be necessary. However, it has been found that, in many locations, ambient BC concentrations are comparable to 0.3 μg/m³ and, thus, temperature compensation is employed to further reduce environmental sensitivity.

The temperature response of three optical cells similar to optical cell 30 was determined by operating each instrument outdoors with the heretofore noted HEPA filter on the inlet for at least 24 hours. In all cases, sample and reference photodiode voltage outputs display a highly linear dependence on the recorded cell temperature. In order to quantify this temperature dependence, the relative change (RC) in each photodiode ratio was calculated as:

$$RC(t) = \frac{V(t) - V(0)}{V(0)}$$

where V(t) is the photodiode voltage at time t, and V(0) is the first voltage logged during the particle-free sampling event.

Figure 10:
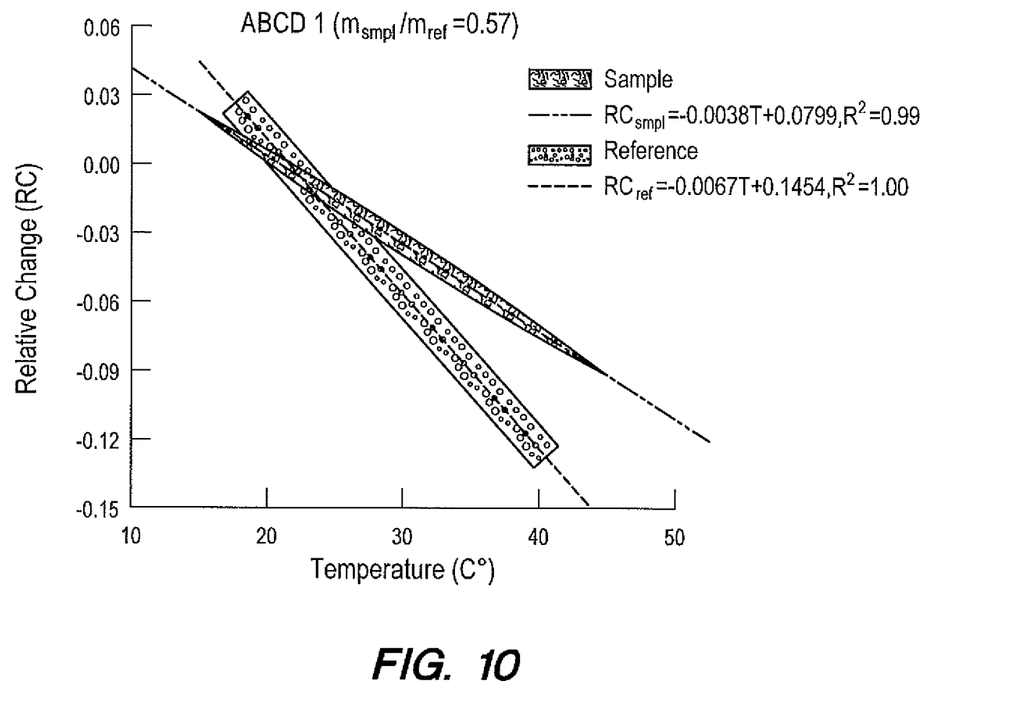
FIG. 10 is a graph depicting the relative change of measurements of an optical cell as a function of temperature.
Figure 11:
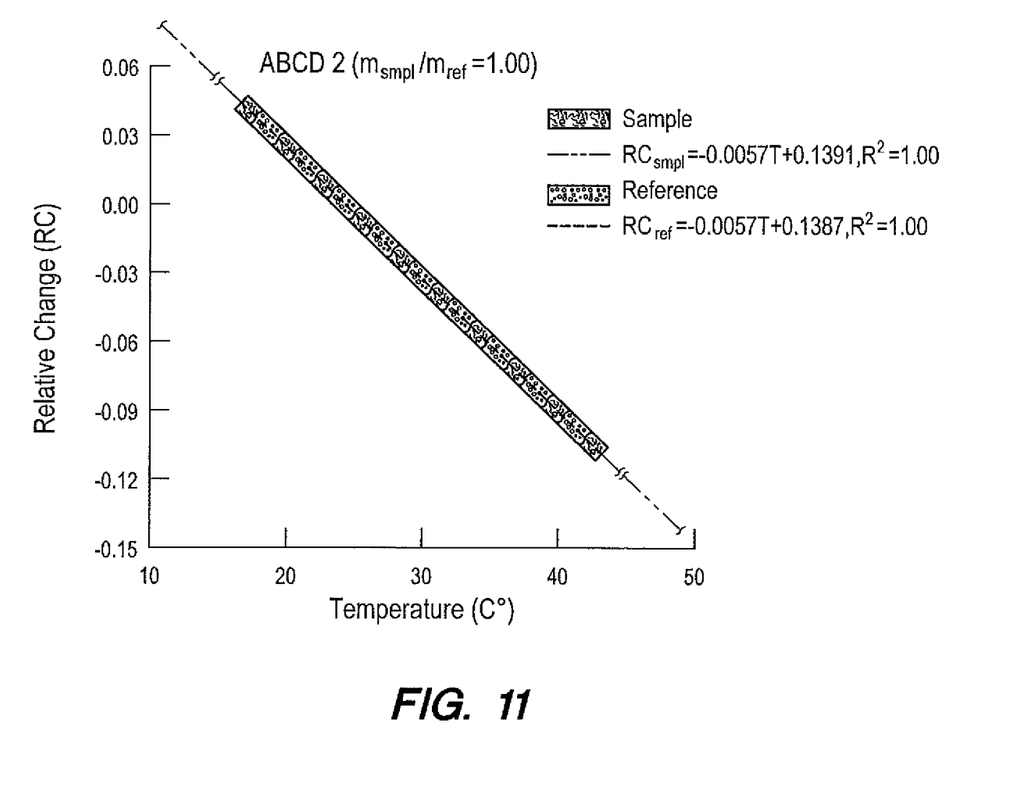
FIG. 11 is a graph depicting the relative change of measurements as a function of temperature for another optical cell.
Figure 12:
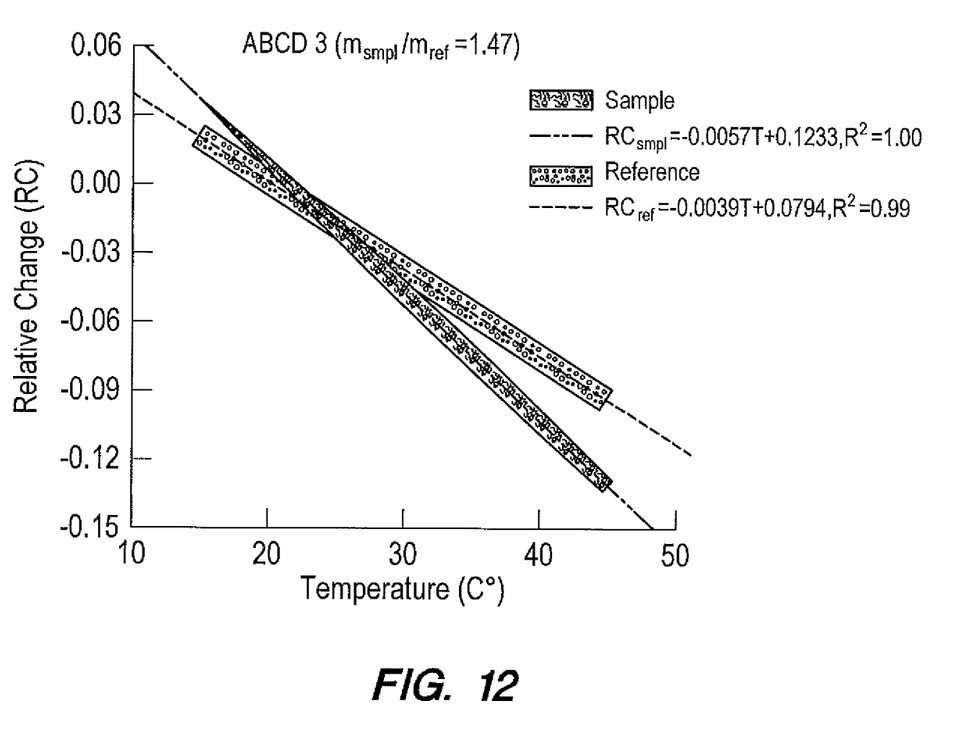
FIG. 12 is a graph depicting the relative change of measurements as a function of temperature for yet another optical cell.

Turning now to FIGS. 10-12, which represent three detector apparatuses similar to apparatus 10 and are identified as: ABCD1, ABCD2, and ABCD3. FIGS. 10-12 are plotted as a function of sensor temperature for the noted three optical cells, and linear regression factors (slope, intercept, and $R^2$) are shown. The temperature sensitivities of an optical cell's sample and reference channels at the sample and reference filters, such as filters 56 and 58 of apparatus 10 (the slopes of the linear regressions $m_{smpl}$ and $m_{ref}$) are not often equal. Therefore, the ratio of these slopes ($m_{smpl}/m_{ref}$, hereinafter referred to as "slope ratio") is often either greater than or less than unity. For example, ABCD1 of FIG. 10 has a slope ratio of 0.57 indicating that the sample voltage output is less temperature sensitive than the reference voltage. Consequently, as the temperature within an optical cell fluctuates over time, the sample and reference voltage outputs do not change at an equal rate. The result is non-zero BC measurements as the effect of changing temperature on the sample voltage output, such as output 76, FIG. 1, is not exactly compensated by the effect of changing temperature on the reference voltage output 78, FIG. 1. For example the optical cell utilized to generate FIGS. 7-9 had a slope ratio of 0.89, and the reference voltage output significantly reduces, but does not completely eliminate, the environmental influence on reported BC concentrations.

In the following equation, the linear regression equations for each photodiode output are set equal to that of the prior equation except that the voltage changes are now evaluated relative to the temperature compensated voltage:

$$RC(t) = \frac{V(t) - V_{comp}(t)}{V_{comp}(t)} = mT(t) + b$$

where the $V_{comp}(t)$ is the temperature-compensated voltage output (V), T(t) is the sample flow temperature (0° C.), and m (° C.$^{-1}$) and b are the slope and intercept of the linear regression, respectively. Rearranging the above equation yields an equation that allows the photodiode voltage, V(t), to be compensated using real time temperature measurements:

$$V_{comp}(t) = \frac{V(t)}{mT(t) + b + 1}$$

BC concentrations calculated using temperature-compensated sample and reference voltage outputs from the above equation are generally significantly less sensitive to temperature fluctuations. It has been observed that there is considerable variability in the temperature sensitivity of optical cells, such as optical cell 30. This is due to the variations in LEDs 64 and 66, photodiodes 72 and 74, and related circuitry found on AUX board 20. The temperature sensitivity and linear regression coefficients found in the above equation were determined uniquely for each individual ABCD optical cell noted in FIGS. 10-12. The slope and intercept for both photodiode outputs, such as photodiodes 72 and 74 of optical cell 30, were stored on SD cards placed in slot 26 and were assigned to each optical cell used to generate FIGS. 10-12. The respective linear regression coefficients for each optical cell were uploaded to MCU 22 to compensate BC measurements in real time as a function of measured temperature. Thus, linear regression factors must be determined uniquely for each ABCD optical cell used to measure airborne light absorbing matter. The same "training period" and compensation may be obtained for relative humidity as an environmental factor.

Figure 13:
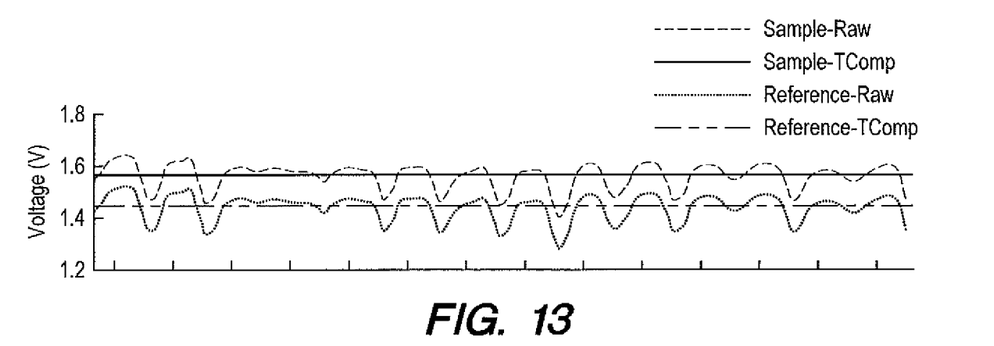
FIG. 13 is a graph depicting response voltages from an apparatus of the present application having a HEPA filter placed on its air inlet, as uncompensated and temperature compensated values.
Figure 14:
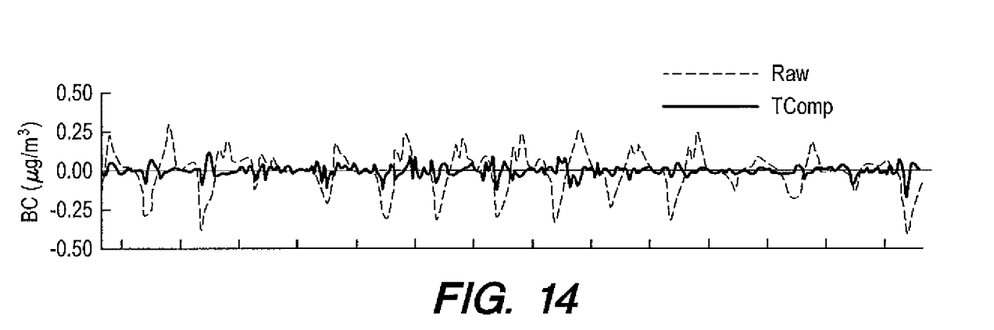
FIG. 14 is a graph showing black carbon concentrations depicted by the optical cell employed with respect to FIG. 13, as uncompensated and temperature compensated valves.
Figure 15:
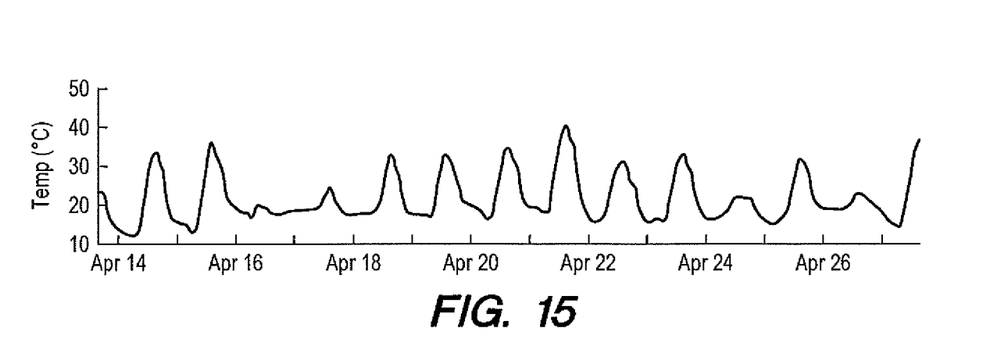
FIG. 15 is a graph depicting optical cell temperature readings during the time period used with the optical cell employed with respect to FIGS. 13 and 14.

FIGS. 13-15 illustrate temperature-compensated (T-Comp) responses as well as uncompensated (Raw) responses for the ABCD utilized to generate the information on FIGS. 7-9. Throughout this trial, temperature-compensated voltage outputs steadily maintained their initial values, FIG. 13, and temperature compensated BC concentrations exhibited a diurnal trend, FIG. 14. Such diurnal trend is typically in the ±0.1 μg/m range (compared to ±0.3 μg/m when uncompensated), with an MAE (mean absolute error) of 0.02 μg/m (compared to 0.1 μg/m when uncompensated). Moreover, FIG. 13 represents reference and sample voltage outputs from an optical cell, such as optical cell 30. FIG. 14 compares uncompensated and temperature-compensated BC concentrations measured by such optical cell. Likewise, FIG. 15 shows cell temperature for the optical cells used to generate the information in FIGS. 13 and 14 over a period of 14 days. All the data gleaned from FIGS. 13-15 were provided on a sixty minute time base. The method of the working example may be employed with the various embodiments 10A-10D of the present application.

While in the foregoing, embodiments of the application have been set forth in considerable detail for the purposes of making a complete disclosure of the application, it may be apparent to those of skill in the art that numerous changes may be made in such details without departing form the spirit and principles of the application.

What is claimed is:

1. An apparatus for determining the optical absorption of matter in an air sample, comprising:
    a case, said case forming a chamber therewithin;
    a first filter positioned in said chamber;
    a second filter positioned in said chamber apart from said first filter;
    a baffle for alternately directing the air sample through said first filter and, subsequently, through said second filter or through said second filter and, subsequently, through said first filter;
    a light source directing light to simultaneously pass through said first and second filters; and
    a first light detector receiving light from said first light source passed through said first filter and generating a first signal therefrom;
    a second light detector receiving light from said light source passed through said second filter and generating a second signal therefrom;
    a temperature sensor in said chamber, said temperature sensor generating a third signal capable of compensating said first and second signals; and
    means for comparing said first, second, and third signals.

2. The apparatus of claim 1 in which said light source comprises:
    a first light source; and
    a second light source, said first light source directing light to pass through said first filter and said second light source directing light to pass through said second filter.

3. The apparatus of claim 1 which additionally comprises:
    a beam splitter positioned between said light source and said first and second filters.

4. The apparatus of claim 1 which additionally comprises a humidity sensor in said chamber, said humidity sensor generating a fourth signal capable of compensating said first and second signals.

5. The apparatus of claim 1 which additionally comprises:
    a pump, said pump delivering the air sample to said case;
    a flow sensor monitoring the flow rate of the air sample through said case; and
    a controller for regulating the flow rate of the sample delivered by said pump to said case.

6. The apparatus of claim 1 which additionally comprises a first orifice through said first filter and a second orifice through said second filter, said first and second orifices each passing said air sample therethrough.

7. The apparatus of claim 5 in which said first and second signals each comprises a voltage signal and said comparing means further comprises:
    an analog-to-digital convertor for receiving said first and second voltage signals and generating corresponding first and second digital signals; and
    a microcontroller unit for receiving said first and second digital signals from said analog-to-digital converter and selectively determining the light absorption of matter and the quantity of light absorbing matter in the air sample.

8. The apparatus of claim 7 in which said light source and said first and second light detectors, said pump, said flow sensor, said controller, said analog-to-digital convertor, and said microcontroller are mounted to a single printed circuit board.

9. An apparatus for determining the optical absorption of matter in an air sample, comprising:
    a case forming a chamber therewithin, said chamber possessing an inlet and an outlet;
    a first filter positioned in said chamber;
    a second filter positioned in said chamber;
    a partition positioned adjacent said first and second filters;
    said first filter and said partition forming a first subchamber in said case;
    said second filter and said partition forming a second subchamber in said case;
    said first and second filters and said partition forming a third subchamber in said casement;
    said first, second, and third subchambers being arranged to allow the air sample to flow through said chamber, in a first order beginning with first subchamber, through said first subchamber, through said first filter, through said third subchamber, through said second filter, through said second subchamber, or in a second order beginning with said second subchamber;
    a first light source directing light to pass through said first filter;
    a first light detector receiving light from said first light source passed through said first filter and generating a first signal therefrom;
    a second light detector receiving light from said second light source passed through said second filter and generating a second signal therefrom; and
    comparator means for determining the ratio value between said first and second signals.

10. The apparatus of claim 9 which additionally comprises a temperature sensor in said chamber, said temperature sensor generating a third signal capable of compensating said ratio value.

11. The apparatus of claim 9 which additionally comprises a humidity sensor in said chamber, said humidity sensor generating a fourth signal capable of compensating said ratio value.

12. The apparatus of claim 11 which additionally comprises a temperature sensor in said chamber, said temperature sensor generating a third signal capable of compensating said ratio value.

13. The apparatus of claim 9 which additionally comprises:
    a pump, said pump delivering the air sample to said case;
    a flow sensor monitoring the flow rate of the air sample through said case; and
    a controller for regulating the flow rate of the sample delivered by said pump to said case.

14. The apparatus of claim 9 which additionally comprises a first orifice through said first filter and a second orifice through said second filter, said first and second orifices each passing said air sample therethrough.

15. The apparatus of claim 9 in which said first and second signals each comprises a voltage signal and said comparator means further comprises:
    an analog-to-digital convertor for receiving said first and second voltage signals and generating corresponding first and second digital signals; and a microcontroller unit for receiving said first and second digital signals from said analog-to-digital converter and determining the quantity of light absorbing matter in the air sample.

16. An apparatus for determining the optical absorption of matter in an air sample, comprising:
   a case, said case forming a chamber therewithin;
   one filter positioned within said chamber, said air sample passing through said one filter;
   another filter, said air sample passing through said another filter subsequent to passage through said one filter;
   a light source directing light through said filter;
   said light source comprising;
   a first light source; and
   a second light source;
   said first light source directing light to pass through said one filter and said second light source directing light to pass through said another filter;
   a light detector for alternately receiving light from said first and second light sources, respectively, passed through said one and another filters, respectively, and generating at least a first signal;
   a temperature sensor for providing a second signal for adjusting said first signal; and
   a means for comparing said first signal to a subsequent signal from said light detector.

17. A method of calibrating an instrument for measuring light absorption of matter in a sample air stream entering the instrument, the instrument including a light source, at least one filter receiving the sample air stream, and at least one light detector for generating a sample signal and a reference signal from light passed through said at least one filter, comprising the steps of:
   placing the at least one filter on the instrument to substantially remove light absorbing matter from said air sample stream;
   passing said sample air stream through said at least one filter for a predetermined period of time;
   directing light from said light source through said at least one filter during said predetermined time period to generate first sample and reference signals, respectively;
   measuring an environmental factor of said sample air stream over said predetermined period of time;
   correlating said environmental factor of said sample air stream with the values of said first sample and first reference signals to obtain an environmental compensation value;
   removing said inlet filter from said instrument;
   passing said sample air stream through said at least one filter;
   directing light from said light source through said at least one filter to generate second sample and reference signals, respectively; and
   applying said environmental compensation factor to said second sample and reference signals to obtain environmental compensated sample and reference signals, respectively; and
   comparing said environmental compensated sample and reference signals to determine the optical absorption of matter in the sample air stream.

18. The apparatus of claim 7 which additionally comprises a beam splitter and said beam splitter is mounted to said single printed circuit board.

\* \* \* \* \*